United States Patent [19]

Ingle

[11] 4,433,300
[45] Feb. 21, 1984

[54] FM DEMODULATOR INCLUDING AUTOMATIC THRESHOLD CONTROL CIRCUIT

[76] Inventor: Frank W. Ingle, 814 Richardson Ct., Palo Alto, Calif. 94303

[21] Appl. No.: 287,478

[22] Filed: Jul. 27, 1981

[51] Int. Cl.³ .............................................. H03D 3/00
[52] U.S. Cl. .................................... 329/136; 329/168; 455/214
[58] Field of Search ............... 329/110, 111, 126, 128, 329/136, 168; 455/214, 337; 73/861.25; 128/663

[56] References Cited

U.S. PATENT DOCUMENTS 3,678,396  7/1972  Hoffman .............................. 329/128
3,863,161  1/1975  Johnson et al. ...................... 329/110

Primary Examiner—Siegfried H. Grimm
Attorney, Agent, or Firm—Warren M. Becker

[57] ABSTRACT

An FM demodulating apparatus with a comparator. The comparator is responsive to a threshold signal and an input signal for providing an output signal which changes polarity each time the difference between the threshold signal and the input signal exceeds a predetermined magnitude. A circuit responsive to the input signal exceeding the threshold signal within a predetermined time period provides an output for controlling the magnitude of the threshold signal.

19 Claims, 6 Drawing Figures

//4,433,300

FM DEMODULATOR INCLUDING AUTOMATIC THRESHOLD CONTROL CIRCUIT

BACKGROUND OF THE INVENTION

The present invention relates to frequency modulation (FM) demodulating apparatus in general and in particular to FM demodulating apparatus comprising an automatic threshold signal controlling circuit for use in an audio frequency Doppler shifted ultrasound blood circulation measuring apparatus.

Ultrasound Doppler instruments are presently used for measuring the velocity of blood in a body. To eliminate the effects of noise, such as instrument-induced noise, from the output signals, it has been the practice to provide on the instruments an operator adjustable control. The control is typically coupled to a potentiometer for setting a threshold signal which must be exceeded by the Doppler shifted input signal in order to obtain an output from the apparatus. Typically, the output is recorded.

A proper setting of the threshold signal requires knowledge of what the appearance of a proper signal should be. This is frequently not known to the operator; such knowledge being gained only by extensive use and operating experience. Moreover, the noise characteristics inherent in different Doppler probes which may be used with a particular instrument may be and often are different, thereby requiring knowledge of what the appearance of a proper output signal would be with each of the Doppler probes used. If the threshold signal is set too high, valuable information concerning the blood circulation or other condition under investigation is not recorded and is therefore lost. If the threshold signal is set too low, excessive noise is recorded with the signals from the condition under investigation which tends to mask the signals under investigation, thereby also causing the useful information to be lost.

Experience has shown that the threshold adjustment for a zero-crossing detector FM demodulator of the type employed in the present invention is baffling to the typical user and that the performance of the circuit depends critically on its proper setting especially when the signal-to-noise ratio is low.

SUMMARY OF THE INVENTION

For the foregoing reasons, a principal object of the present invention is a zero-crossing detector FM demodulating apparatus comprising means responsive to an input signal exceeding a predetermined magnitude within a predetermined time period for automatically controlling the magnitude of a threshold signal.

Still another object of the present invention is an apparatus as described above, wherein the input signal produces an output signal which changes polarity and the threshold signal controlling means comprises means responsive to said changes in the polarity of said output signal and a reference signal for changing the magnitude of said threshold signal each time said output signal changes polarity in said predetermined time period.

Still another object of the present invention is an apparatus as described above wherein both the magnitude and the polarity of said threshold signal is changed in response to said output signal.

Still another object of the present invention is an apparatus as described above wherein said threshold signal controlling means comprises means for measuring the amplitude of said input signal.

Still another object of the present invention is an apparatus in which said amplitude measuring means comprises means for measuring the average or the peak amplitude of said input signal.

Still another object of the present invention is an apparatus as described above wherein said amplitude measuring apparatus comprises means for analyzing the pulse height of said input signals for controlling said threshold signal.

BRIEF DESCRIPTION OF THE DRAWING

The above and other objects, features and advantages of the present invention will become apparent from the following detailed description of the accompanying drawings in which.

DETAILED DESCRIPTION OF THE DRAWINGS

Figure 1:
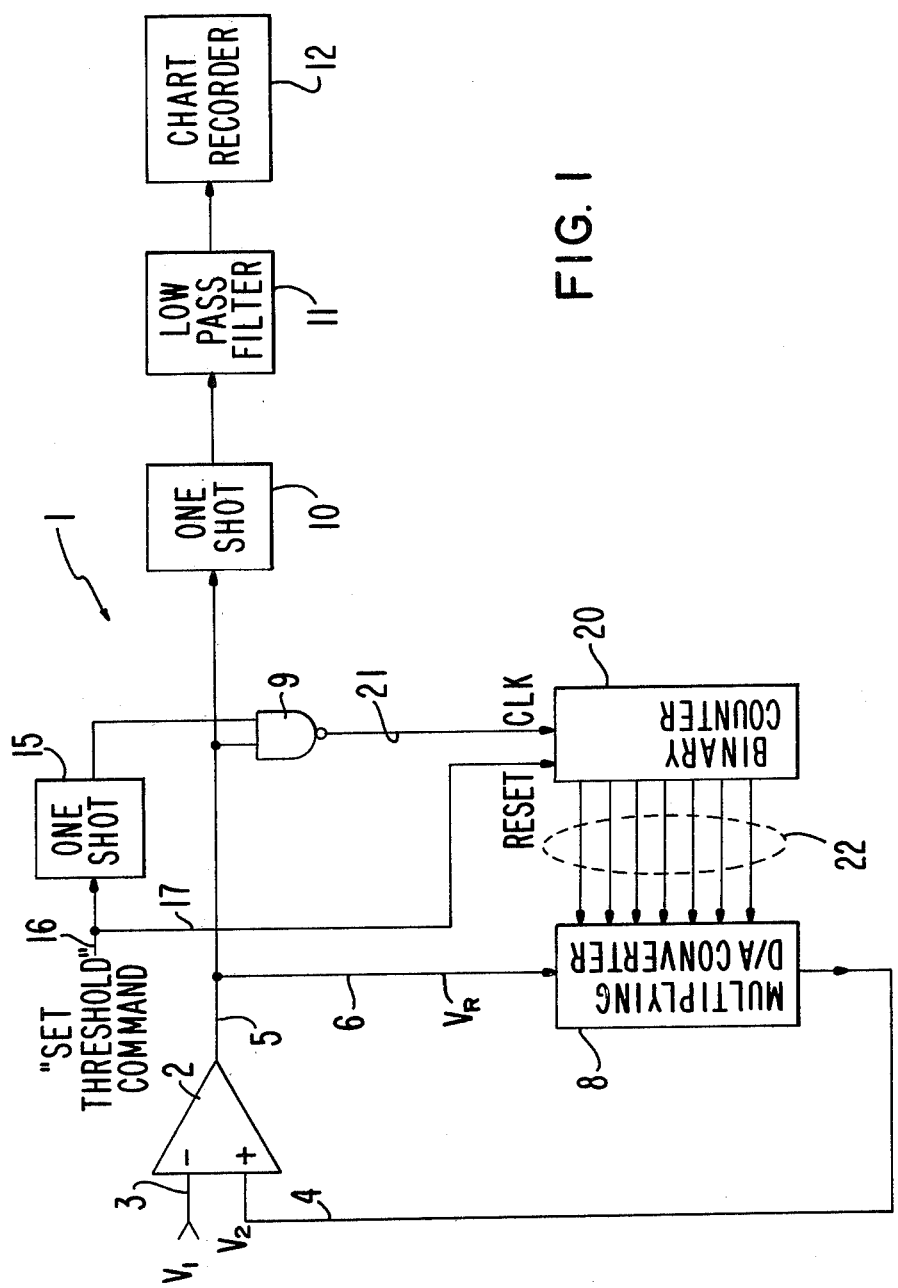
FIGS. 1–6 are block diagrams of alternative embodiments of the present invention.

Referring to FIG. 1 there is provided in accordance with the present invention an autothreshold circuit for automatically controlling the setting of a threshold signal in a zero-crossing detector FM demodulator, designated generally as 1. In the autothreshold circuit 1 there is provided a comparator 2 having a negative input and a positive input. The negative input is provided for receiving on a line 3 a high level audio frequency Doppler shifted input signal $V_1$. The positive input is provided for receiving on a line 4 a threshold signal $V_2$. The output of the comparator 2 is provided on a line 5.

Coupled to line 5 and the output of the comparator 2 there is provided a multiplying digital-to-analog converter 8, a two-input NAND gate 9 and a one-shot multivibrator 10. The converter 8 is coupled to the output of the comparator 2 by means of a line 6 for receiving a voltage reference signal $V_R$.

Coupled to the output of the one-shot 10 there is provided a low pass filter 11 and coupled to the output of the low pass filter 11 there is provided a chart recorder 12. The one-shot 10, filter 11 and recorder 12 are provided for determining and recording a voltage proportional to the average switching frequency of comparator 2.

Coupled to the other input of the two-input NAND gate 9 there is provided a one-shot multivibrator 15. The input to the one-shot multivibrator 15 is provided by a line 16. In practice the line 16 is coupled to a pushbutton or other type of control for providing a "set threshold" command to the one-shot 15, as will be described in detail below.

The line 16 is also coupled, by means of a line 17, to the reset input of a binary counter 20. The clock input to the counter 20 is provided by a line 21 coupled to an inverting output of the gate 9. The output of the binary counter 20 is provided by means of a plurality of lines 22 which are coupled to corresponding inputs of the digital-to-analog converter 8.

In operation, the comparator 2 changes state each time the value of $(V_2-V_1)$ changes sign. If $V_2=0$, the converter 2 converts a sine wave of any amplitude to a square wave of the same frequency. The one-shot multivibrator 10 and low pass filter 1 form a tachometer whose output voltage depends linearly on an input frequency. If $V_2=0$, this system operates correctly with no noise present at the input $V_1$. If the signal amplitude does not exceed the noise amplitude by a wide margin however, the noise will cause extra zero-crossings and will also mask some of the signal zero-crossings. The standard solution is to choose $V_2 \neq 0$ and adjustable by means of an external control. In the absence of any DC signal component, this setting may be chosen to provide any degree of immunity to input noise. Doing this necessarily rejects small amplitude desired signals also, of course. But, since the number of zero-crossings per second caused by noise depends exponentially on the value of $V_2$, it can be appreciated that the adjustment is both critical and difficult to make manually.

Accordingly, in operation, when the "set threshold" command occurs on the line 16, the binary counter 20 is reset to all 0's by means of the reset signal on the line 17. $V_R$ appearing on the line 6 is the saturated output of the comparator 2 and is approximately ±4 volts in a typical embodiment. The multiplying D/A converter 8 multiplies $V_R$ times the value (binary count/full scale binary count) of the contents of the binary counter 20. Thus, when the binary counter 20 is reset, the value of $V_2$ becomes 0 volts.

The time during which the counter 20 receives an output from the comparator 2 is determined by the time that the gate 9 is enabled by the output of the one-shot 15. During the setting of the threshold voltage signal $V_2$, it is required that the only input signal $V_1$ at the input of the comparator 2 be noise that is generated by the Doppler system; i.e., no noise or other signal may be present which is generated by the desired Doppler source. In the present application the Doppler source is a probe used for measuring blood circulation in the body.

Since initially the threshold voltage is 0 ($V_2=0$), the first noise induced zero-crossing will cause the comparator 2 to change state. With the gate 9 enabled by the "set threshold" command on the line 16, this transition is counted by the counter 20. The multiplying D/A converter 8 then changes $V_2$ to the value of $V_R$ (1/binary full scale). The sign of $V_2$ is the same as that of the comparator output, opposite to the sign of the input signal which induces it. The net result is thus a comparator with hysteresis. Noise at the input must therefore have a peak-to-peak amplitude exceeding 2 $V_2$ in order to affect the comparator output. As the threshold setting process continues, each noise induced "zero-crossing" detected increases the threshold required for subsequent noise to trigger the comparator. The rate of observed transitions quickly goes nearly to 0, however, a set time of 0.4 seconds was found adequate to complete the process and compatible with the patience of the operator.

When the set time ends, the one-shot 15 disables the gate 9 and the hysteresis level is stored digitally in the counter 20 for as long as power is maintained to the unit. At this level of hysteresis, noise is reduced to a level determined by the noise characteristics and the set time, which are invariant. It is assumed that the noise amplitude does not change with time. If it does, the set process must be repeated to obtain the proper threshold value.

In practice the noise level is affected to a small extent by the acoustic loading of the receiving crystal. For an approximate auto setting, the probe with gel on it should be held still and the "set threshold" command button connected to line 16 pushed. For best performance, the probe should be directed into the body at a quiet site for the autosetting.

Figure 2:
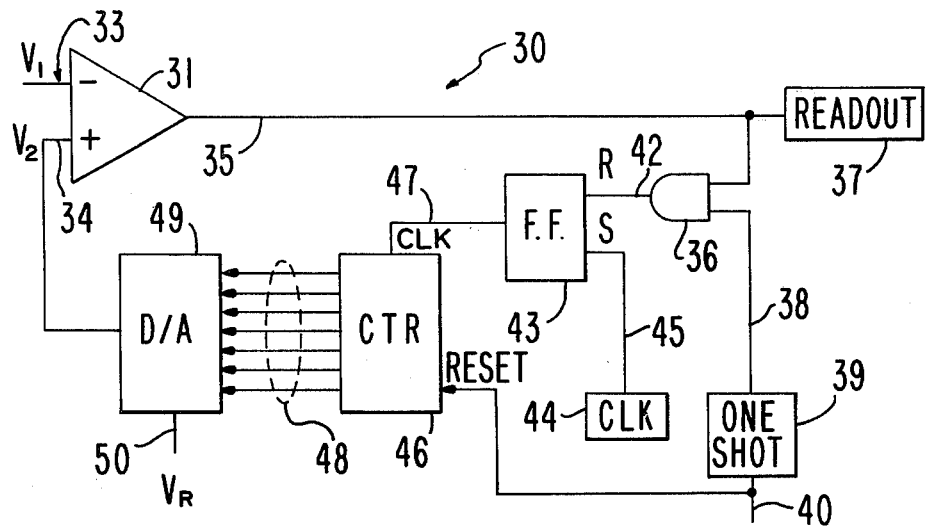

Referring to FIG. 2, there is provided in an alternative embodiment of the present invention an autothreshold circuit 30. In the circuit 30 there is provided a comparator 31 having a negative and a positive input. The negative input is coupled to an input line 33 for receiving a voltage input signal $V_1$. The positive input is coupled to a line 34 for receiving a voltage threshold signal $V_2$. The output of the comparator 31 is provided on a line 35. The line 35 is coupled to one input of a dual input AND gate 36 and to a readout circuit 37. The readout circuit 37 comprises conventional tachometer circuits for recording the average frequency of the comparator 31 output as described above with respect to the one-shot 10, low pass filter 11 and chart recorder 12 of the embodiment of FIG. 1.

Coupled to the second input of the AND gate 36 by means of a line 38 there is provided a one-shot 39. The one-shot 39 is provided with a "set threshold" command input on a line 40 which corresponds to the "set threshold" command input line 16 coupled to the input of the one-shot 15 of FIG. 1. Coupled to the output of the gate 36 by means of a line 42 there is provided the reset input of a flip-flop 43. A clock 44 for providing clock pulses on a line 45 is coupled to the set input of the flip-flop 43. The output of the flip-flop 43 is coupled to a counter circuit 46 on a line 47. The output of the counter circuit 46 is provided by means of a plurality of lines 48 to corresponding inputs of a digital-to-analog converter circuit 49. A voltage reference signal $V_R$ is provided to the D/A converter 49 on a line 50. The output of the D/A converter 49 provides the voltage threshold signal $V_2$ to the comparator 31 on the line 34.

In operation, with a "set threshold" command input signal on the line 40 to the one-shot 39, the counter 46 is reset and the gate 36 is enabled for the period of the one-shot 39, e.g. 0.4 seconds. With the gate 36 enabled, the output from the comparator 31 is gated through the gate 36 to the reset input of the flip-flop 43. With the flip-flop 43 reset, a clock pulse will set the flip-flop. Consequently, the circuit of FIG. 2 counts one external clock pulse only if a signal crossing has occurred since the last clock pulse was counted. Accordingly, the number of zero-crossings that will be detected will be a function of the rate of the clock 44.

Each time the zero-crossing is counted the counter 46 is advanced increasing the magnitude of the input of the D/A converter 49 which is multiplied by the reference signal $V_R$ on line 50 to give a threshold signal $V_2$ on line 34. As described above with respect to FIG. 1, if the reference $V_R$ changes polarity as would be the case if coupled to the output of the comparator 31, the threshold signal $V_2$ also changes magnitude and polarity.

Figure 3:
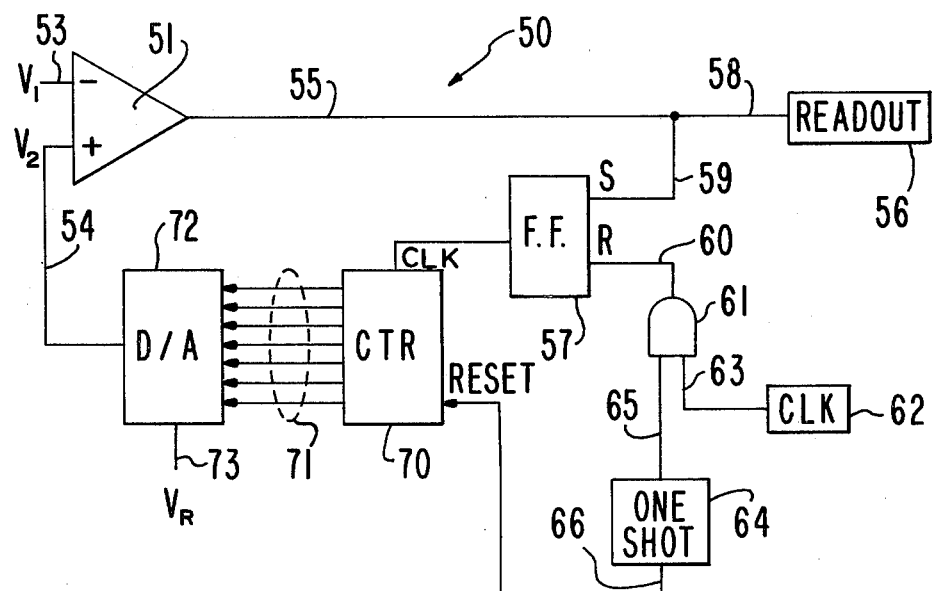

Referring to FIG. 3, there is provided in another embodiment of the present invention similar to the embodiment described above with respect to FIG. 2, an autothreshold circuit designated generally as 50. In the circuit 50 there is provided a comparator 51 having a negative input and a positive input. The negative input receives an input signal $V_1$ on a line 53. The positive input receives a threshold voltage $V_2$ on a line 54. The output of the comparator 51 is provided on an output line 55. The output line 55 is coupled to the input of the readout circuit 56, and the set input of a flip-flop 57 by means of a pair of lines 58 and 59 respectively. The readout circuit 56 is identical to the readout circuit 37 described above with respect to FIG. 2, and typically comprises a one-shot, a low pass filter, and a chart recorder corresponding to the one-shot 10, low pass filter 11 and chart recorder 12 described above with respect to FIG. 1.

Coupled to the reset input of the flip-flop 57 by means of a line 60, there is provided the output of a two-input AND gate 61. One input of the AND gate 61 is coupled to the output of a clock circuit 62 by means of a line 63. The second input of the AND gate 61 is coupled to the output of a one-shot 64 by means of a line 65. The one-shot 64 is provided with a set input line 66 for receiving a set command signal as described above with respect to the set command signal received on the input line 40 of the one-shot 39 of the circuit of FIG. 2.

The output of the flip-flop 57 is coupled to a binary counter 70. The output of the counter 70 is coupled by means of a plurality of lines 71 to a corresponding number of input lines of a digital-to-analog converter 72. The converter 72 is provided on a line 73 with a voltage reference signal $V_R$ corresponding to the voltage reference signal $V_R$ on the line 50 of the D/A converter 49 described above with respect to FIG. 2. The output of the D/A converter 72 is the voltage threshold signal $V_2$ appearing on the line 54.

In operation, the output of the comparator 51 sets the flip-flop 57 after each resetting of the flip-flop 57 by the clock 62 during the period determined by the output of the one-shot 64 as described above with respect to the circuit of FIG. 2. With each setting of the flip-flop 57 the counter 70 is advanced. Each time that the counter 70 is advanced there is generated a corresponding change in the magnitude of the threshold voltage $V_2$ on the output of the converter 72. If the voltage reference signal on the line 73 changes polarity as described above with respect to the circuit of FIG. 1, the voltage threshold signal $V_2$ also changes polarity.

The operations of the circuits of FIGS. 2 and 3 are slightly more complex than the circuit of FIG. 1; however, they provide similar output results if the frequency of the clock circuits 44 and 62 respectively exceeds the frequency of the audio frequency Doppler shifted input signal $V_1$.

Figure 4:
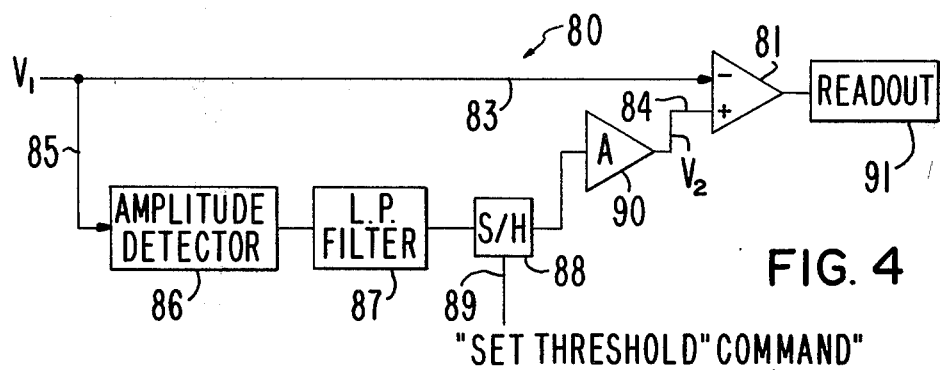

Referring to FIG. 4, there is provided in another embodiment of the present invention an autothreshold circuit designated generally as 80. In the circuit 80 there is provided a comparator 81 having a negative input and a positive input. The negative input is provided for receiving on a line 83 a Doppler shifted audio input signal $V_1$. The positive input is provided for receiving on a line 84 a voltage threshold signal $V_2$. Coupled to the line 83 by means of a line 85 there is provided an amplitude detector circuit 86. The output of amplitude detector circuit 86 is coupled to the input of a low pass filter 87. The output of the filter 87 is coupled to the input of a sample-and-hold circuit 88. The sample-and-hold circuit 88 is provided to receive on a line 89 a "set threshold" command input signal corresponding to the "set threshold" command input signals described above with respect to FIGS. 1, 2 and 3. The output of the sample-and-hold circuit 88 is coupled to an amplifier 90 for providing the voltage threshold signal $V_2$ on the line 84.

In operation, when it is desired to set the voltage threshold signal $V_2$, a signal on the "set threshold" command input line 89 enables the sample-and-hold circuit 88 to be in its "sample" mode. The amplitude detector 86 and low pass filter 87 develop an output signal for the sample-and-hold circuit 88 corresponding to the average amplitude of the input signal $V_1$. The setting of the sample-and-hold circuit 88 by means of the signal on the line 89 samples the output of the low pass filter 87 and holds the signal which is thereafter amplified in the amplifier 90, for setting the voltage threshold signal $V_2$.

Coupled to the output of the comparator 81 there is provided a readout circuit 91 which corresponds to the readout circuits 37 and 56 of FIGS. 2 and 3 respectively.

Figure 5:
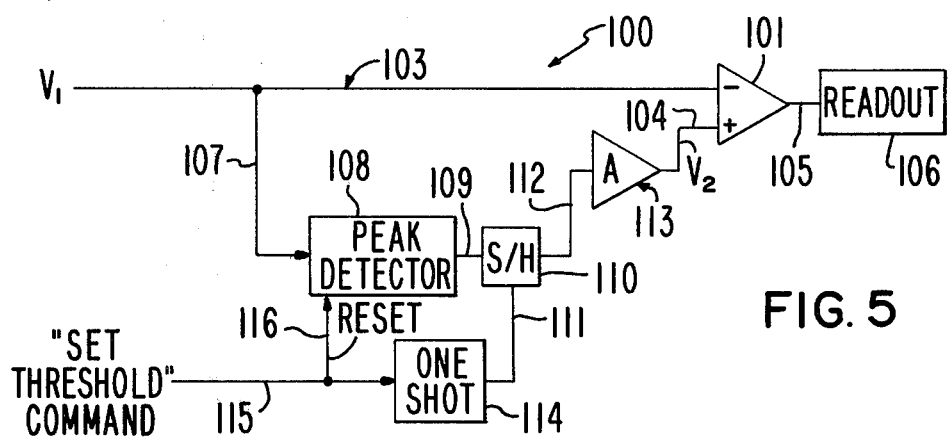

Referring to FIG. 5, there is provided another embodiment of an autothreshold circuit according to the present invention designated generally as 100. In the circuit 100 there is provided a comparator circuit 101, having a negative input and a positive input. The negative input is provided for receiving on a line 103 an audio frequency Doppler shifted input signal $V_1$. The positive input is provided for receiving on a line 104 a threshold signal $V_2$. The output of the comparator 101 is coupled by means of a line 105 to the input of a readout circuit 106. The readout circuit 106 is identical to the readout circuits 37, 56 and 91 of the circuits of FIGS. 2, 3 and 4 respectively.

Coupled to the line 103 by means of a line 107, there is provided a peak detector 108. The output of the peak detector 108 is coupled by means of a line 109 to the input of a sample-and-hold circuit 110. The sample-and-hold circuit 110 is provided with an input for providing on a line 111 from a one-shot 114 a "sample" signal. A "set threshold" command signal is received by the one-shot 114 on a line 115. The "set threshold" command signal is also coupled to the reset input of the peak detector 108 by a line 116. The "set" signal on the line 115 resets the peak detector 108 to zero and triggers the one-shot 114. The one-shot 114 enables the sample-and-hold 110 to be in the "sample mode" for a fixed period of time. During this time the output of the peak detector 108 is equal to the peak value of the largest peak on line 107 since reset. At the end of the fixed period the sample-and-hold 110 enters the "hold mode" and its output does not change until the next reset signal or until the power is interrupted. The "set threshold" command signal received on the line 115 corresponds to the set input signal received on the lines 16, 40, 66 and 89 of the circuits of FIGS. 1-4. Coupled to the output of the sample-and-hold circuit 110 by means of a line 112, there is provided an amplifier 113. The amplifier 113 is provided for providing the voltage reference signal $V_2$ on the line 104.

In operation, the peak detector 108 provides an output on the line 109 corresponding to the magnitude of the peak value attained by the input signal $V_1$ during the period of one shot 114. The sample-and-hold circuit 110 samples and holds the output of the peak detector 108, as described above, for providing an output on the line 112. The amplifier 113, which typically has a gain of approximately 1, amplifies the output of the sample-and-hold circuit 110 for providing the threshold voltage $V_2$ on the line 104.

Figure 6:
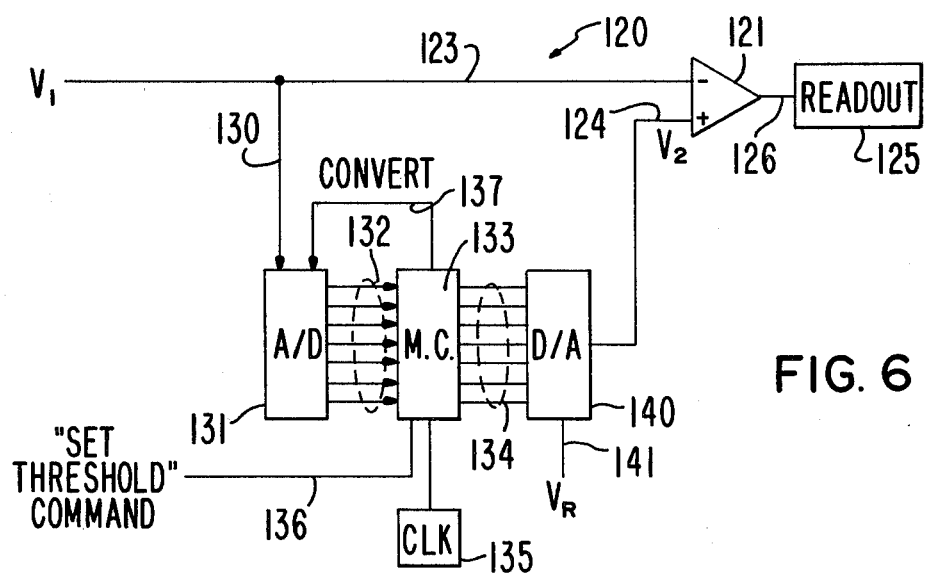

Referring to FIG. 6 there is provided, in an alternative embodiment of the present invention, an autothreshold circuit designated generally as 120. In the circuit 120 there is provided a comparator circuit 121. Comparator circuit 121 has a negative input and a positive input. The negative input is provided for receiving on a line 123 an audio frequency Doppler shifted input signal $V_1$. The positive input of the circuit 121 is provided for receiving on a line 124 a threshold signal $V_2$. The output of the comparator circuit 121 is coupled on the input of the readout circuit 125 by means of a line 126. Readout circuit 125 is identical to and provides the function of the readout circuits 37, 56, 91 and 106 of the circuits of FIGS. 2-5.

Coupled to the line 123 by means of a line 130, there is provided an analog-to-digital converting circuit 131. The output of the A/D converter 131 is provided on a plurality of lines 132. The lines 132 are coupled to corresponding inputs of a conventional microcomputer 133. Microcomputer 133 is provided with a plurality of output lines 134. A clock circuit 135 is provided coupled to the circuit 133 for providing clock pulses to the circuit 133. The circuit 133 is also provided with an input for receiving on a line 136 a "set threshold" command input signal corresponding to the "set threshold" command input signals receiving on the lines 40, 66, 89 and 115 of the circuits of FIGS. 2-5. On a line 137, the circuit 133 provides a convert signal to the A/D converter 131.

The plurality of output lines 134 of the circuit 133 are coupled to a corresponding number of inputs of a digital-to-analog converting circuit 140. The circuit 140 also receives on a line 141 a voltage reference signal $V_R$. The voltage reference signal $V_R$ corresponds to the voltage reference signal $V_R$ described above with respect to FIGS. 1-3. The D/A converter 140 is provided for providing the voltage threshold voltage $V_2$ on the line 124.

In operation the microprocessor circuit 133, in response to a "set threshold" command signal on the line 136, generates a convert signal on the line 137. The convert signal on the line 137 enables the A/D converter 131 to convert the analog input signal $V_1$ to a digital signal. Using clock pulses from the clock circuit 135 in a conventional manner, the microprocessor 133 analyses the output of the A/D converter 131 for providing a digital output corresponding to an input signal of a predetermined amplitude. A computation is made in the microcomputer based on the statistical properties of the input signal of the threshold voltage necessary to reduce the number of threshold crossing to a predetermined number per second. A digital signal corresponding to this threshold voltage is then generated. The digital output of the microprocessor 133 is then provided to the digital-to-analog converter 140 and is multiplied by the voltage reference signal $V_R$ for providing the voltage threshold signal $V_2$ as described above with respect to the circuits of FIGS. 1-3.

While several embodiments incorporating the present invention are described, it is contemplated that still other embodiments of the present invention may be made without departing from the spirit and scope thereof. Accordingly, it is intended that the embodiments described be used only for purposes of illustrating the present invention and that the scope of the invention be determined by reference to the claims hereinafter provided and their equivalents.

What is claimed is:

1. In an FM demodulating apparatus, having a threshold signal setting period and an operation period, an automatic threshold control circuit comprising:
   means responsive to a threshold signal and an input signal due to noise on an input line during said threshold signal setting period for providing an output signal which changes polarity each time the difference between the amplitude of said threshold signal and said input noise signal changes polarity; and
   means responsive to said input noise signal exceeding a predetermined magnitude within said threshold signal setting period for controlling the magnitude of said threshold signal.

2. An apparatus according to claim 1 wherein said threshold signal controlling means comprises:
   means responsive to changes in said polarity of said output signal and a reference signal for changing the magnitude of said threshold signal each time said output signal changes polarity in said threshold signal setting period.

3. An apparatus according to claim 1 wherein said threshold signal controlling means comprises:
   means responsive to changes in said polarity of said output signal and a reference signal for changing the magnitude and polarity of said threshold signal each time said output signal changes polarity within said threshold signal setting period.

4. An apparatus according to claim 1 wherein said output signal comprises a reference signal and said threshold signal controlling means comprises means responsive to said reference signal and said changes in polarity of said output signal for changing the magnitude and polarity of said threshold signal each time said output signal changes polarity within said threshold signal setting period.

5. An apparatus according to claim 1 wherein said threshold signal controlling means comprises:
   means for providing a reference signal;
   counting means for counting the changes in the polarity of said output signal within said threshold signal setting period;
   means for gating said output signal into said counting means for said threshold signal setting period; and
   means responsive to said counting means and said reference signal for providing said threshold signal with a magnitude proportional to said reference signal and the number of times said output signal changes polarity within said threshold signal setting period.

6. An apparatus according to claim 5 wherein said reference signal comprises said output signal and said threshold signal providing means comprises means for providing said threshold signal with a polarity corresponding to the polarity of said output signal.

7. An apparatus according to claim 5 wherein said threshold signal providing means comprises a multiplying digital-to-analog converting means responsive to said reference signal and a count contained within said counting means for providing said threshold signal.

8. An apparatus according to claim 1 comprising means for indicating the number of times said output signal changes polarity.

9. An apparatus according to claim 8 wherein said indicating means comprises recording means.

10. An apparatus according to claim 8 wherein said indicating means comprises means for providing an output corresponding to an average of the number of times said output signal changes polarity within a predetermined time period.

11. An apparatus according to claim 1 wherein said threshold signal controlling means comprises:
    means for providing clock pulses and means responsive to said clock pulses and each time said input signal exceeds said threshold signal by said predetermined magnitude within said threshold signal setting period for providing a count signal corresponding to the number of times said input signal exceeds said threshold signal within said threshold signal setting period as a function of the rate of said clock pulses; and means responsive to said count signal providing means for setting said threshold signal.

12. An apparatus according to claim 11 wherein said count signal providing means comprises:
   a flip-flop;
   gate means coupled to a means for enabling said gate means for said threshold signal setting period and responsive to said input signal exceeding said threshold signal for resetting said flip-flop;
   means coupling said flip-flop to said clock pulse providing means for setting said flip-flop; and
   means for counting the number of times said flip-flop is set and reset during said threshold signal setting period.

13. An apparatus according to claim 11 wherein said count signal providing means comprises:
   a flip-flop;
   means responsive to said input signal exceeding said threshold signal for setting said flip-flop;
   gate means coupled to a means for enabling said gate means for said threshold signal setting period and responsive to said clock pulses for resetting said flip-flop; and
   means for counting the number of times said flip-flop is set and reset during said threshold signal setting period.

14. An apparatus according to claim 1 wherein said output signal providing means comprises a first input for receiving said input noise signal and a second input for receiving said threshold signal and said threshold signal controlling means comprises means for providing said threshold signal having an amplitude proportional to the number of said changes in polarity of said output signal during said threshold signal setting period.

15. An apparatus according to claim 14 wherein said threshold signal providing means comprises means for providing a threshold signal corresponding to the average amplitude of said input signal during said threshold signal setting period.

16. An apparatus according to claim 15 wherein said threshold signal providing means comprises a low pass filter, a sample-and-hold circuit, and an amplifier for sampling and holding said average amplitude signal and providing said threshold signal proportional to it.

17. An apparatus according to claim 14 wherein said threshold signal providing means comprises means for providing said threshold signal corresponding to the peak amplitude of said input signal during said threshold signal setting period.

18. An apparatus according to claim 17 wherein said threshold signal providing means comprises a sample-and-hold circuit and amplifier for sampling and holding said peak amplitude signal and providing said threshold signal proportional to it.

19. An apparatus according to claim 14 wherein said threshold signal providing means comprises:
   analog-to-digital converting means;
   computing means for providing an output computed from the magnitude of the output of said analog-to-digital converting means; and
   digital-to-analog converting means for providing an analog signal having a magnitude corresponding to the output of said computing means.

* * * * *